United States Patent
Ikami

(10) Patent No.: US 7,773,223 B2
(45) Date of Patent: Aug. 10, 2010

(54) IMAGE SCANNING APPARATUS AND IMAGE SCANNING METHOD

(75) Inventor: Seishi Ikami, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 201 days.

(21) Appl. No.: 12/049,018

(22) Filed: Mar. 14, 2008

(65) Prior Publication Data

US 2008/0240747 A1 Oct. 2, 2008

(30) Foreign Application Priority Data

Mar. 27, 2007 (JP) ............................. 2007-082090

(51) Int. Cl.
*G01N 21/64* (2006.01)
(52) U.S. Cl. ..................... 356/417; 250/458.1; 356/432
(58) Field of Classification Search .................. 356/417
See application file for complete search history.

(56) References Cited

U.S. PATENT DOCUMENTS 5,702,915 A * 12/1997 Miyamoto ................... 435/32
6,331,441 B1 * 12/2001 Balch et al. .................... 506/15
6,570,158 B2 * 5/2003 Feygin ........................ 250/332

FOREIGN PATENT DOCUMENTS

JP 2005-283322 A 10/2005

* cited by examiner

*Primary Examiner*—F. L Evans
(74) *Attorney, Agent, or Firm*—Sughrue Mion, PLLC

(57) ABSTRACT

An image scanning apparatus has an organic CMOS image sensor mounted in a base, and a photoreceptive surface of the image sensor is exposed on a top side of the base. A subject is placed directly on the photoreceptive surface, and the subject and the photoreceptive surface are covered up with a cover light-tightly. Thus the image sensor detects only chemiluminescent light from the subject. As for a fluorochrome-labeled subject, the subject placed directly on the photoreceptive surface is irradiated with excitation light from a light source mounted in the cover. The image sensor is provided with a filter for blocking the excitation light from its photoelectric conversion layers, so the image sensor detects only fluorescent rays generated from the excited fluorochrome-labeled subject. The image scanning apparatus needs no redundant space in perpendicular direction to the photoreceptive surface.

19 Claims, 12 Drawing Sheets

IMAGE SCANNING APPARATUS AND IMAGE SCANNING METHOD

FIELD OF THE INVENTION

The present invention relates to an image scanning apparatus that captures an image from a subject containing a biological substance, the image representing a reactive condition of the biological substance. The present invention relates also to an image scanning method for the image scanning apparatus.

BACKGROUND OF THE INVENTION

Apparatuses that capture an image of a subject placed in a chassis while illuminating the subject with a light source have conventionally been used in many different application fields. In the field of biochemistry, an imaging apparatus, which uses a chemiluminescent substance or a fluorescent substance as a labeling material and reads out luminescence or fluorescence of the labeling material to detect gene sequences, level of gene expression, separation, identification or molecule weight of protein, or evaluate characteristics, has been known for example from JPA2005-283322.

Concretely, for example, after adding a fluorescent coloring material or fluorochrome, to a solution containing DNA fragments, the DNA fragments are electrophoresed on a gel support. Alternatively, DNA fragments are electrophoresed on a gel support that contains a fluorescent coloring material. Thereafter, the gel support is soaked in a solution containing a fluorescent coloring material, to label the electrophoresed DNA fragment. Then the gel support is irradiated with excitation light to excite the fluorescent coloring material to radiate fluorescent light, and the fluorescent light is captured to produce an image. Based on the subsequent image, a DNA distribution on the gel support is detectable.

In another alternative, DNA fragments are denatured after being electrophoresed on a gel support. Next, the denatured DNA fragments are at least partially transferred to a transfer support such as a nitrocellulose film through the southern blotting method. Then, the denatured DNA fragments are hybridized with a probe, which is preparated by fluorochrome-labeling of such DNA or RNA that is complementary to the target DNA, so that only the fragments of the complementary DNA to the fluorochrome-labeled DNA or RNA probe are sorted to be labeled. Thereafter, the fluorescent coloring material is excited with the excitation light, and the radiated fluorescent light is captured as an image, to detect a distribution of the target DNA on the transfer support.

The above-mentioned prior art captures a luminescent or fluorescent image by converging light from the gel support or the transfer support through an optical system onto an image sensor. However, the chemiluminescent light and the fluorescent light are so feeble and attenuate to such a low level through the optical system that it takes a long exposure time to obtain a satisfactory image even though the optical system uses lens elements of small f-numbers. That is, the optical system adversely affects the sensitivity of the image sensor to the chemiluminescent or fluorescent light in the prior art.

Furthermore, the subject such as the gel support or the transfer support is conventionally placed horizontally in the chassis in order to prevent deviation and improve operability. On the other hand, the optical system and the image sensor are oriented vertically, i.e. perpendicularly to the subject. Therefore, the subject and the optical system need certain spacing between them, which enlarges the height of the apparatus. However, considering recent trend to minimization and lightness of hardware devices of various fields, compactness is desirable also in the biochemical field.

SUMMARY OF THE INVENTION

In view of the foregoing, a primary object of the present invention is to provide an image scanning apparatus that is thin and superior in sensitivity to chemiluminescent and fluorescent light and thus reduces the requisite time for exposure, and thus reduces adverse influence caused by dark current.

The present invention also has an object to provide an image scanning method for such an image scanning apparatus.

According to the present invention, an image scanning apparatus for capturing an image from a subject containing biological substances, the image representing reaction of the biological substances, comprises a base having a supporting side for supporting the subject thereon; an image sensor having a photoreceptive surface and at least a photoelectric conversion layer that generates electric charge corresponding in amount to light entering from the photoreceptive surface, the image sensor being mounted in the base with the photoreceptive surface exposed on the supporting side of the base, so the subject placed on the supporting side is in contact with the photoreceptive surface; and a cover for covering up the photoreceptive surface in a light-tight fashion.

Preferably, an image scanning apparatus further comprises a light source mounted in the cover, the light source being opposed to the photoreceptive surface and emitting light toward the photoreceptive surface while the cover is in a closed position covering up the photoreceptive surface.

The light source preferably illuminates the whole area of the photoreceptive surface uniformly.

In order to capture an image from a dyed subject, the light source emits white light toward the photoreceptive surface, and the image sensor captures an image from light transmitted through the subject as placed on the photoreceptive surface. In that case, it is preferable to provide the image scanning apparatus with an image processing device for discriminating saturated pixels of the image sensor after the image-capturing, and setting an output value of the saturated pixels to a predetermined level.

In a case where the biological substances of the subject are labeled with a fluorescent pigment, the light source emits excitation light toward the subject, whereas the image sensor captures an image from fluorescent light that is radiated from the biological substances as being excited by the excitation light. In that case, the image sensor comprises a band elimination filter for cutting only a wavelength band of the excitation light.

Preferably, the image scanning apparatus further comprises a temperature adjusting device for adjusting the image sensor to a set temperature, e.g. the temperature suitable for activating the biological substances.

The photoelectric conversion layer of the image sensor is preferably an organic photoelectric conversion layer. More preferably, the image sensor comprises a plural number of organic photoelectric conversion layers, which are sensitive to light components of different wavelength ranges from one layer to another. The organic photoelectric conversion layers are stacked in such a sequence that one sensitive to the shorter wavelength range is located closer to the photoreceptive surface.

As an alternative, another image scanning apparatus of the present invention comprises a base for supporting the subject on its supporting side; a cover for covering up the supporting side of the base in a light tight fashion; and an image sensor having a photoreceptive surface and at least a photoelectric conversion layer that generates electric charge corresponding in amount to light entering from the photoreceptive surface, the image sensor being mounted in the cover so that the photoreceptive surface is in contact with the subject placed on the supporting side of the base when the cover is in a closed position covering up the supporting side of the base. The photoelectric conversion layer of the image sensor is preferably an organic photoelectric conversion layer.

According to a preferred embodiment, the image scanning apparatus having the image sensor in its base further comprises a light source mounted in the base, the light source being opposed to the photoreceptive surface and emitting light toward the photoreceptive surface while the cover is in the closed position.

Still another image scanning apparatus of the present invention comprises a base for supporting the subject on its supporting side; a cover for covering up the supporting side of the base in a light tight fashion; a first image sensor mounted in the base with its photoreceptive surface exposed on the supporting side of the base, the first image sensor having at least an organic photoelectric conversion layer to output a first analog image signal corresponding to a light component received from the subject that is placed on the supporting side in contact with the photoreceptive surface; and a second image sensor mounted in the cover so that the photoreceptive surface is brought into contact with the subject placed on the supporting side of the base when the cover is set to a closed position covering up the supporting side of the base, the second image sensor having at least an organic photoelectric conversion layer to output a second analog image signal corresponding to a light component received from the subject.

The image scanning apparatus having the first and second image sensors further comprises a device for producing a digital composite image from the first and second analog image signals.

According to the present invention, an image scanning method using an image sensor having at least an organic photoelectric conversion layer comprises steps of:

placing a subject containing biological substances on a supporting side of a base;

brining a cover to a closed position covering up the supporting side of the base in a light tight fashion; and driving the image sensor in the closed position of the cover, the image sensor being mounted in at least one of the base and the cover so that a photoreceptive surface of the image sensor is in contact with the subject in the closed position of the cover.

The image scanning apparatus does not need any optical system for forming an image of the subject, because the subject is put in direct contact with the photoreceptive surface of the image sensor during the imaging. Therefore, the light from the subject will not suffer the attenuation through the optical system, so the image scanning apparatus of the invention achieves high-sensitive imaging. Because of the improved sensitivity to chemiluminescent or fluorescent light, it becomes possible to shorten the exposure time. Furthermore, no redundant space is necessary in the perpendicular direction to the photoreceptive surface of the image sensor, which has conventionally been necessary for forming an image on the photosensitive surface through the optical system. Thus, the image scanning apparatus of the present invention can be made thinner than conventional ones.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
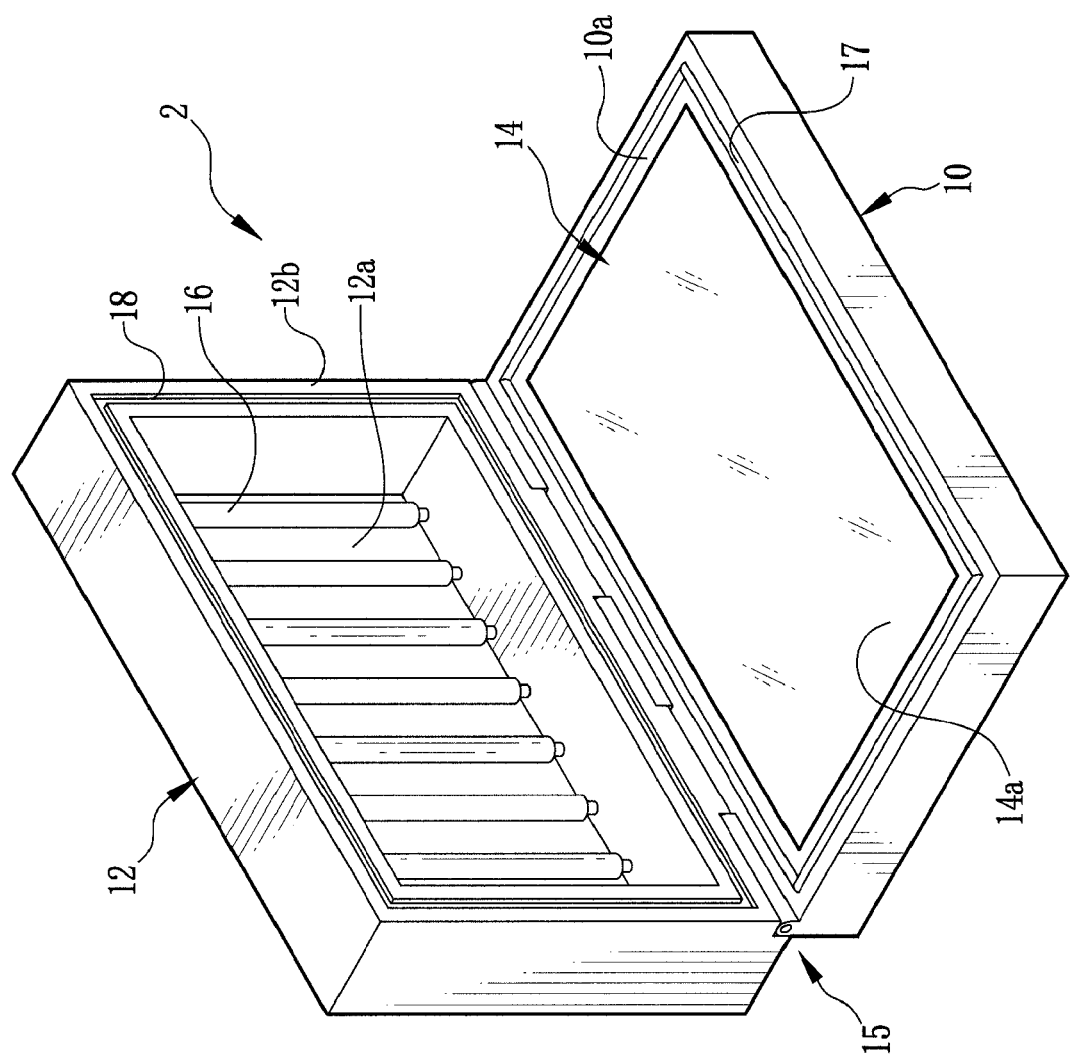
FIG. 1 is a schematic perspective view of an image scanning apparatus.

As shown in FIG. 1, an image scanning apparatus 2 is constituted of a base 10 for supporting a subject, and a cover 12 for covering up the subject on the base 10. The base 10 is shaped a substantially rectangular plate, whereas the cover 12 is shaped into a substantially parallelepiped box with an open side. An organic CMOS image sensor 14 is mounted in the base 10. The image sensor 14 has a photoreceptive surface 14a exposed on a top side or supporting side 10a of the base 10. The photoreceptive surface 14a is a rectangular surface of 10 cm×15 cm in this example, but its area size and shape are not limited to this example.

In the image scanning apparatus 2, a subject that is emitting light as being in contact with a chemiluminescent substance or a fluorochrome-labeled subject that is labeled with a fluorescent coloring material is directly placed on the photoreceptive surface 14a. Then the image sensor 14 is driven to scan the whole area of the photoreceptive surface 14a, thereby to obtain image data representative of a chemiluminescent or fluorescent condition of the subject. For example, the subject may be a solution or a gel support, which contains biological substances like protein, enzyme, nucleic acid, DNA, RNA, or a membrane film, onto which any of these biological substances are transferred. The subject may also be a living animal, like a mouse or a rat, which is administrated with a luminescent or fluorescent reagent for the sake of in vivo imaging.

The cover 12 is coupled to the base 10 through a hinge 15, so that the cover 12 may be turned open to expose the photoreceptive surface 14a as shown in FIG. 1. In a closed position shown in FIG. 2, the open side of the cover 12 is opposed to the top side 10a of the base 10, and the cover 12 covers up the photoreceptive surface 14a light-tightly, shielding the image sensor 14 from extraneous light other than the chemiluminescent or fluorescent light from the subject.

A plural number of ultraviolet fluorescent tubes 16 are mounted on an inside surface 12a of the open side of the cover 12, so that they are opposed to the photoreceptive surface 14a in the closed position, to illuminate the photoreceptive surface 14a with ultraviolet rays of 400 nm or less in wavelength. In order to illuminate the whole area of the photoreceptive surface 14a uniformly with the ultraviolet rays, the ultraviolet fluorescent tubes 16 are arranged at equal intervals. The ultraviolet fluorescent tubes 16 constitute a light source device for exciting the fluorochrome-labeled subject. After the fluorochrome-labeled subject is placed on the photoreceptive surface 14a, the image scanning apparatus 2 lights the ultraviolet fluorescent tubes 16 to irradiate the fluorescently-labeled subject to excite it. Note that the wavelength of the excitation light is not limited to the above example, but may be another appropriate value insofar as it can excite the subject.

The base 10 has a sealing member 17 on its top side 10a, framing around the photoreceptive surface 14a, whereas the cover 12 has a groove 18 in its rim 12b in opposition to the groove 18. The sealing member 17 protrudes cylindrically upward from the top side 10a of the base 10 and elastically fits in the groove 18 when the cover 12 is closed. As being elastically deformed to make a tight contact with the groove 18, the sealing member 17 ensures light-tightness of the cover 12.

In order to apply the image scanning apparatus 2 to the in vivo imaging where a living animal like a mouse or a rat is the subject, an internal space of the image scanning apparatus 2, which is formed as the cover 12 is closed, is filled with hypnotic gas or anesthetic gas, so that the animal will not move. In that case, the elastically deformable sealing member 17 also ensures air tightness of the internal space, preventing leakage of the sleep-inducing gas or anesthetic gas. The sealing member 17 may be made of a resin material such as a silicone gum, which is preferably opaque or black to enhance the light blocking property. The sealing member 17 may alternatively be provided on the cover 12. Preferably, the base 10 or the cover 12 is provided with an inlet for injecting the sleep-inducing gas or anesthetic gas and a valve member for controlling the gas injection.

Figure 2:
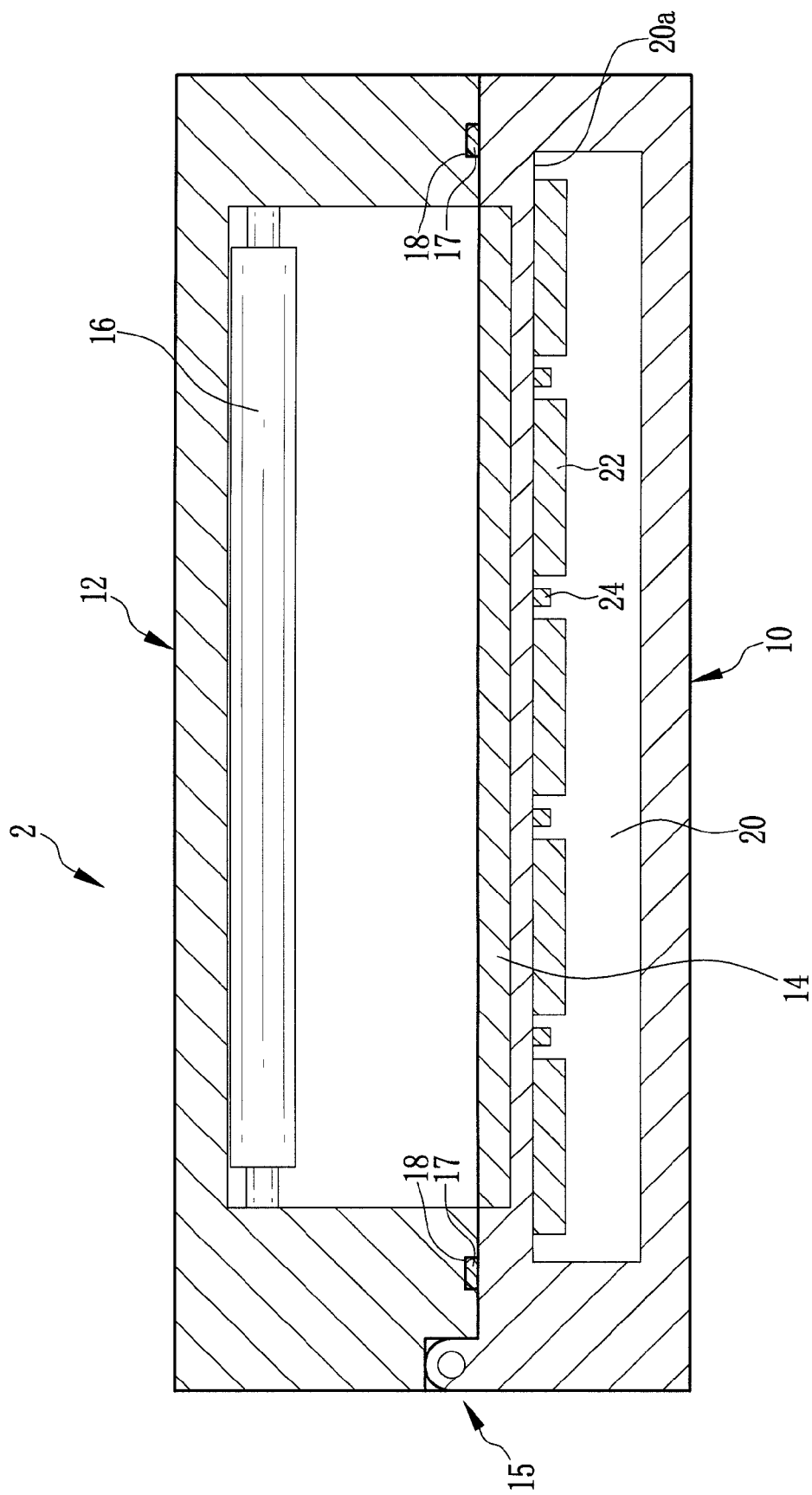
FIG. 2 is a vertical section of the image scanning apparatus.

As shown in FIG. 2, the base 10 has a hollow 20 on the backside of the image sensor 14. The hollow 20 has a top surface 20a that is parallel to the photoreceptive surface 14a and larger than the photoreceptive surface 14a. A plural number of peltiert elements 22 and temperature sensors 24 are mounted on the top surface 20a of the hollow 20, and are arranged in an array such that the peltiert elements alternate their cooling sides and heating sides like a chessboard. The image scanning apparatus 2 controls the peltiert elements 22 while monitoring temperature through the temperature sensors 24, to adjust the image sensor 14 to a set temperature.

The temperature sensors 24 may be thermocouples, resistance-temperature detectors, thermistor, or other devices insofar as they can measure the temperature. The temperature of the image sensor 14 is preferably adjusted according to what kind of subject is placed on the photoreceptive surface 14a. For example, in a case where the subject contains a human-related biological substance, the temperature of the image sensor 14 is preferably adjusted to be in a range from 35° C. to 37° C., which is suitable for activity of the biological substance, i.e. the temperature about the same as its body temperature.

Adjusting the temperature of the image sensor 14 to the range from 35° C. to 37° C. involves a risk that dark current increases to cause deterioration of image quality. However, since the subject is placed directly on the photoreceptive surface 14a, the requisite exposure time is so shortened that the dark current would not remarkably affect the image quality even in the above-mentioned temperature range.

Figure 3:
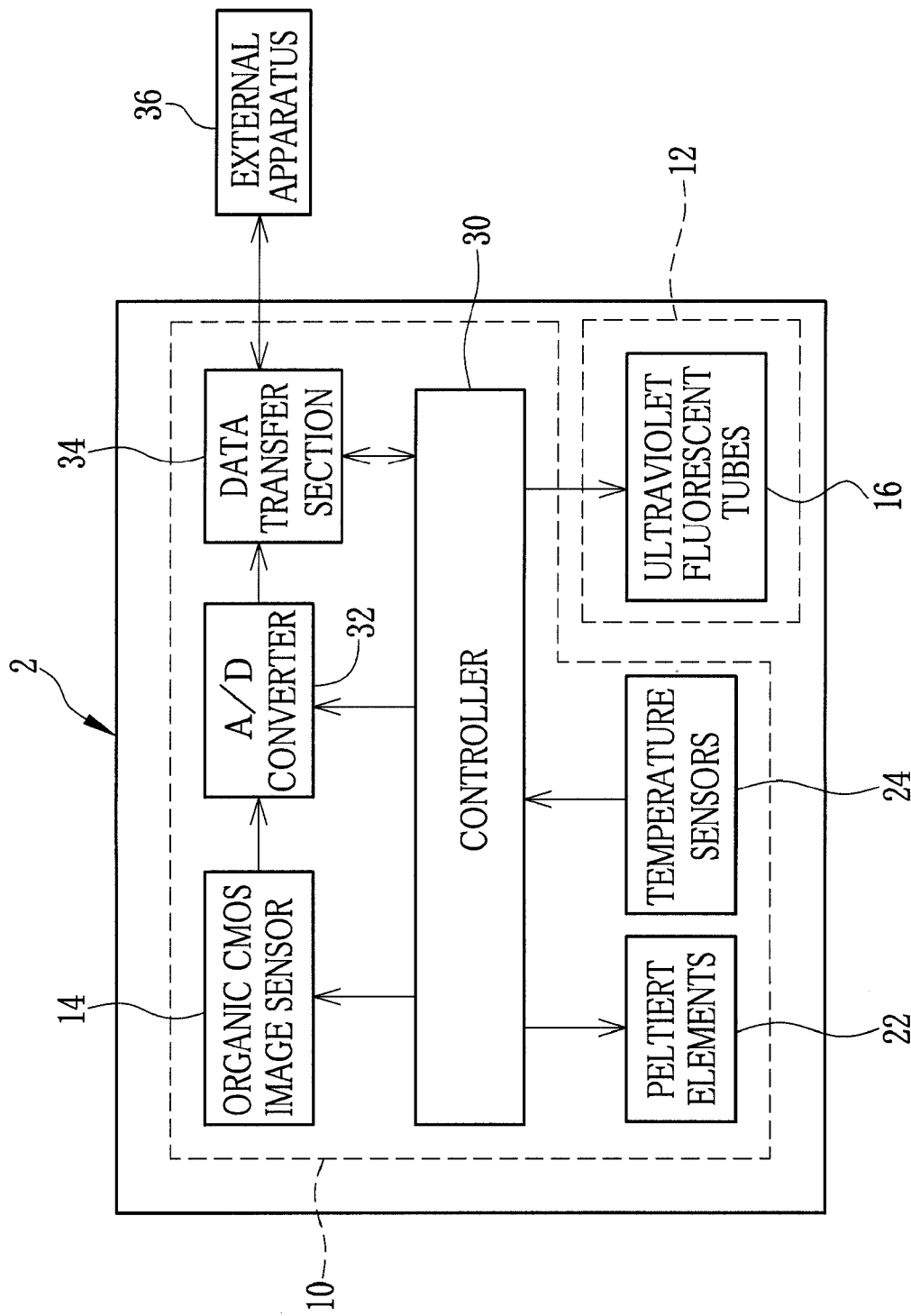
FIG. 3 is a block diagram illustrating an electric structure of the image scanning apparatus.

FIG. 3 shows an electric structure of the image scanning apparatus 2 according to a first embodiment. Beside the image sensor 14, the peltiert elements 22 and the temperature sensors 24, the base 10 is provided with a controller 30 for controlling respective components of the image scanning apparatus 2, an A/D converter 32 for converting analog image signals as obtained by the image sensor 14 into digital image data, and a data transfer section 34 for sending and receiving data to and from external apparatuses 36.

The controller 30 is connected to the image sensor 14, and sends a drive signal to the image sensor 14, to control image-capturing of the image sensor 14. The controller 30 is also connected to the peltiert elements 22 and the temperature sensors 24. The controller 30 monitors outputs from the temperature sensors 24 and changes voltages applied to the peltiert elements 22 in accordance with the outputs from the temperature sensors 24, i.e. temperature levels at respective measurement points of the temperature sensors 24, so that the temperature of the image sensor 14 is adjusted to a constant level in the whole area of the photoreceptive surface 14a. Thereby, shading of the image, which could be caused by temperature unevenness, is suppressed.

The controller 30 is further connected to the ultraviolet fluorescent tubes 16 that are mounted to the cover 12. The controller 30 controls ON/OFF of the ultraviolet fluorescent tubes 16. As described above, the ultraviolet fluorescent tubes 16 are turned on to capture an image from the fluorochrome-labeled subject. The electric connection between the base 10 and the cover 12 may be provided through flexible printed circuit boards or the like that are conducted from the base 10 through the hinge 15 to the cover 12.

The A/D converter 32 receives the analog image signals from the image sensor 14, converts it into the digital image data, and sends the digital image data to the data transfer section 34.

The image scanning apparatus 2 is connected through the data transfer section 34 to the external apparatuses 36 such as personal computers. The data transfer section 34 transfers the image data to the external apparatuses 36, receives control signals and other data from the external apparatuses 36, and input them to the controller 30. It is possible to provide the base 10 with a storage device like a hard disc drive, so as to store the image data temporarily in the image scanning apparatus 2.

Figure 4:
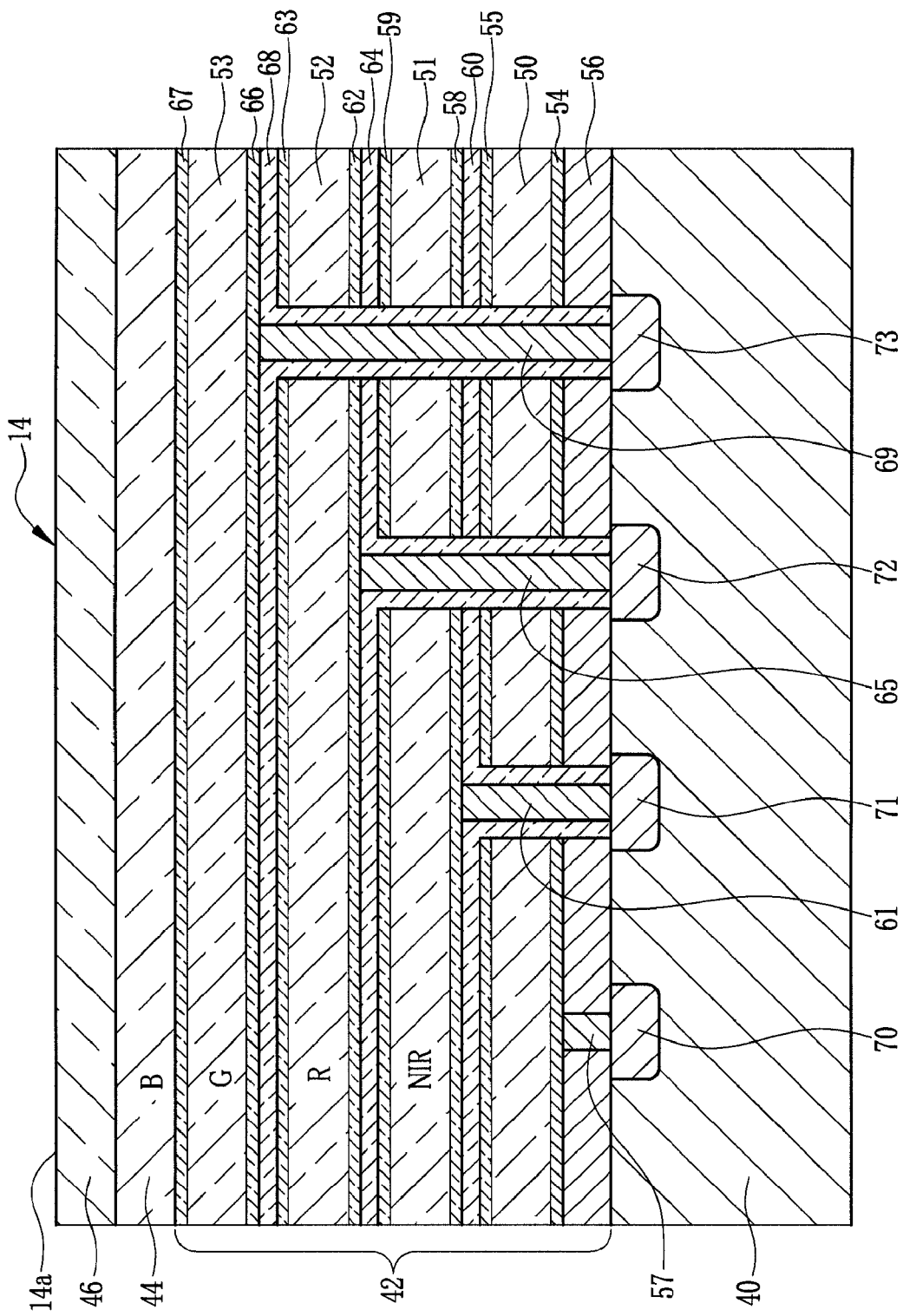
FIG. 4 is a fragmentary section of one pixel of an organic CMOS image sensor.

FIG. 4 shows an enlarged section of one pixel of the image sensor 14. The image sensor 14 is constituted of a silicone substrate 40 in which a CMOS structure is formed, photoelectric conversion layers 42 stacked on the silicone substrate 40, a filter layer 44 formed atop the photoelectric conversion layers 42, and a SELFOC lens array (trade mark) 46 formed atop the filter layer 44. For example, the size of each pixel of the image sensor 14 is 2 μm to 50 μm, and more preferably 2 μm to 20 μm.

The photoelectric conversion layers 42 comprises a near-infrared sensitive photoelectric conversion film 50 that is sensitive to near-infrared light, a red sensitive photoelectric conversion film 51 that is sensitive to red light, a green sensitive photoelectric conversion film 52 that is sensitive to green light, and a blue sensitive photoelectric conversion film 53 that is sensitive to blue light. These films 50 to 53 are organic photoelectric conversion films and output electric charges of such amounts that correspond to the volumes of incident light beams to which the respective films are sensitive. Hereinafter, these organic photoelectric conversion films 50 to 53 will be referred to as the NIR photoelectric conversion film 50, the R photoelectric conversion film 51, the G photoelectric conversion film 52 and the B photoelectric conversion film 53.

The photoelectric conversion films 50 to 53 are stacked atop another in this sequence from the bottom, so that the light of shorter wavelength is sensed faster. For example, the NIR photoelectric conversion film 50 senses the light of 700 nm to 2500 nm as the near-infrared light, the R photoelectric conversion film 51 senses the light of 600 nm to 700 nm as the red light, the G photoelectric conversion film 52 senses the light of 500 nm to 600 nm as the green light, and the B photoelectric conversion film 53 senses the light of 400 nm to 500 nm as the blue light. Preferably, the respective films 50 to 53 have absorption factors of not less than 50% to respective peak wavelengths of their sensitive wavelength ranges.

The photoelectric conversion films 50 to 53 are composed of organic compounds, e.g. acene group such as perylene, teracene, pentacene and pyrene, and their derivatives; conjugated polymers such as polyacetylene derivatives, polythiophene derivatives, poly(3-alkylthiophene) derivatives and poly(3,4-ethylene dioxy thiophene) derivatives having thiophene rings, polyphenylene vinylene derivatives, polyphenylene derivatives and polyphenylene vinylene derivatives having benzene rings, polypyridine derivatives having nitrogen, polypyrrole derivatives, polyaniline derivates, polyquinoline derivatives; oligomers such as dimethyl sexithiophene and quarterthiophene; organic molecules such as copper phthalocyanine derivatives; discotic crystal such as triphenylene derivative; smectic liquid crystal such as phenyl naphthalene derivatives and benzothiazole derivatives; liquid crystal polymers such as poly(9,9-dialkyl fluorene-bithiophene) copolymer; and other organic compounds such as copper phthalocyanine derivatives, zinc phthalocyanine derivatives, polythiophene derivatives, polyparaphenylene derivatives and merocyanine dye.

The photoelectric conversion films 50 to 53 may contain general dyes or pigments. Exemplars of applicable dyes are rhodamine-B, eosin-Y, coumalin etc. Exemplars of applicable pigments are azo pigment, squarylium pigment, azulenium pigment, phthalocyanine pigment etc. To control electro-conductivity, the photoelectric conversion films 50 to 53 may contain appropriate dopant. We can refer to $I_2$, $Br_2$, $Cl_2$, ICl, $BF_3$, $PF_5$, $H_2SO_4$, $FeCl_3$ and TCNQ (tetra-cyano-quinodimethane) as acceptor type dopants, as well as Li, K, Na, Eu as donor type dopants. Also alkyl sulfonate and alkyl benzene sulfonate, which are face-active agents, are applicable as the dopant.

As described above, the image sensor 14 senses light of different wavelength ranges for the near-infrared (NIR) light, the red (R) light, the green (G) light and the blue (B) light by the respective photoelectric conversion films 50 to 53, and captures images of NIR, R, G and B respectively on the photoelectric conversion films 50 to 53, to get full-color (RGB) image data and infrared image data. Thus, the image sensor 14 senses the NIR, R, G and B light components at each pixel, so it can captures an image of higher resolution than that captured by a conventional image sensor where RGB color filters are arranged in front of their pixels so that each pixel senses a light component of a specified wavelength range that passes through the color filter.

The near-infrared photoelectric conversion film 50 is provided with a membrane electrode 54 on its lower side and a membrane electrode 55 on its upper side. Between the lower side membrane electrode 54 and the silicone substrate 40 is provided an isolation film 56. The membrane electrode 54 is connected to the silicone substrate 40 through a via plug 57 that is put through the isolation film 56.

The red photoelectric conversion film 51 is provided with a membrane electrode 58 on its lower side and a membrane electrode 59 on its upper side. Between the lower side membrane electrode 58 and the upper side electrode 55 of the near-infrared sensitive photoelectric conversion layer 50 is provided an isolation film 60. The membrane electrode 58 is connected to the silicone substrate 40 through a via plug 61 that is put through the near-infrared sensitive photoelectric conversion layer 50, the electrodes 54 and 55 and the isolation films 56 and 60.

The green photoelectric conversion film 52 is provided with a membrane electrode 62 on its lower side and a membrane electrode 63 on its upper side. Between the lower side membrane electrode 62 and the upper side electrode 59 of the red sensitive photoelectric conversion layer 51 is provided an isolation film 64. The membrane electrode 62 is connected to the silicone substrate 40 through a via plug 65 that is put through the near-infrared sensitive photoelectric conversion layer 50, the red sensitive photoelectric conversion layer 51, the electrodes 54, 55, 58 and 60 and the isolation films 56, 60 and 64.

The blue photoelectric conversion film 53 is provided with a membrane electrode 66 on its lower side and a membrane electrode 67 on its upper side. Between the lower side membrane electrode 66 and the upper side electrode 63 of the red sensitive photoelectric conversion layer 51 is provided an isolation film 68. The membrane electrode 66 is connected to the silicone substrate 40 through a via plug 69 that is put through the near-infrared sensitive photoelectric conversion layer 50, the red sensitive photoelectric conversion layer 51, the green sensitive photoelectric conversion layer 52, the electrodes 54, 55, 58, 60, 62 and 63 and the isolation films 56, 60, 64 and 68.

Except the membrane electrode 54 under the near-infrared sensitive photoelectric conversion layer 50, the membrane electrodes 55, 58, 59, 62, 63, 66 and 67 are light-permeable transparent electrodes. As the transparent electrode, ITO (indium tin oxide), IZO (indium zinc oxide), ZnO (zinc oxide), $SnO_2$ (tin oxide) are usable.

Except the isolation film 56 under the near-infrared sensitive photoelectric conversion layer 50, the isolation films 60, 64 and 68 are light permeable transparent isolation films. To form the transparent isolation film, silicon nitride, silicone oxide, glass, polyethylene, polyethylene terephthalate, polyether sulfone, polypropylene are usable. Particularly, silicon nitride film formed by plasma CVD (chemical vapor deposition) is preferable because it is excellently dense and transparent.

In those parts of the silicone substrate 40 which have contact with the via plugs 57, 61, 65 and 69, charge storage portions 70, 71, 72 and 73 are formed in correspondence with the respective photoelectric conversion films 50 to 53. The electric charge generated on the near-infrared sensitive photoelectric conversion layer 50 is transferred to the charge storage portion 70 through the via plug 57 as a voltage is applied across the corresponding membrane electrodes 54 and 55. The electric charge generated on the near-infrared sensitive photoelectric conversion layer 50 is transferred to the charge storage portion 70 through the via plug 57 as a voltage is applied across the corresponding membrane electrodes 54 and 55. The electric charge generated on the red sensitive photoelectric conversion layer 51 is transferred to the charge storage portion 71 through the via plug 61 as a voltage is applied across the corresponding membrane electrodes 58 and 59. The electric charge generated on the green sensitive photoelectric conversion layer 52 is transferred to the charge storage portion 72 through the via plug 65 as a voltage is applied across the corresponding membrane electrodes 63 and 63. The electric charge generated on the blue sensitive photoelectric conversion layer 53 is transferred to the charge storage portion 73 through the via plug 69 as a voltage is applied across the corresponding membrane electrodes 66 and 67. The silicone substrate 40 is further provided with a well-known transfer circuit though it is not shown in the drawings. Through the transfer circuit, the charges stored in the respective charge storage portions 70 to 73 are transferred to be output as the analog image signals.

The filter layer 44 constitutes a band elimination filter that cuts the ultraviolet rays radiated from the ultraviolet fluorescent tubes 16, i.e. the excitation light. During the image capturing, the filter 44 lets pass only chemiluminescent or fluorescent light radiated from the subject, and blocks the ultraviolet rays from entering the photoelectric conversion layers 42. Thus, background noises caused by the ultraviolet rays are suppressed, improving the detection sensitivity to the chemiluminescent or fluorescent light from the subject.

The SELFOC lens array 46 has a lot of rod lenses arranged in correspondence with the respective pixels. The SELFOC lens array 46 not only conducts the incident light to the photoelectric conversion layers 42, but also functions as a protector film for the photoelectric conversion layers 42. The above-described structure of the image sensor 14 is described in more detail in many prior documents, for example, in JPA 2007-12796.

Figure 5:
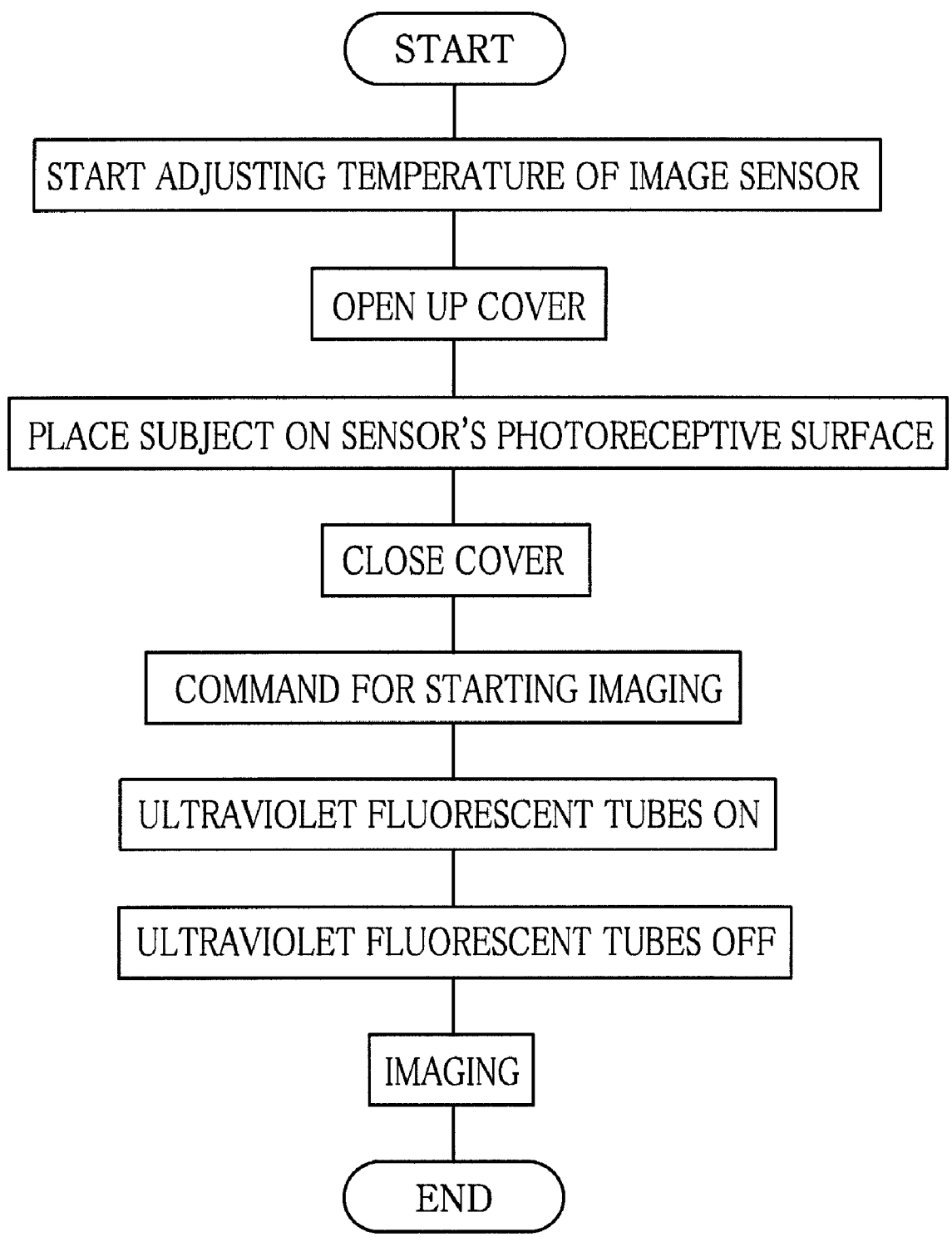
FIG. 5 is a flowchart illustrating a sequence of procedures for capturing an image of a fluorochrome-labeled subject.

Now the operation of the image scanning apparatus 2 in a case of image-capturing from a fluorochrome-labeled subject will be described with reference to the flowchart of FIG. 5.

First, a not-shown power switch of the image scanning apparatus 2 is turned on. Then the controller 30 starts controlling the peltiert elements 22 and the temperature sensors 24 to adjust the temperature of the image sensor 14.

Adjusting the temperature of the image sensor 14 suppresses the shading that would be caused by temperature unevenness, and also controls the temperature of the subject as it is in contact with the image sensor 14, so as to activate biological substances contained in the subject. Adjusting the temperature of the image sensor 14 in advance as soon as the power switch is turned on also contributes to maintaining body temperature of an animal placed as the subject on the photoreceptive surface 14a while the animal is under hypnosis and tends to lower its temperature.

After powering the image scanning apparatus 2, the cover 12 is opened to expose the photoreceptive surface 14a. Then the subject is placed directly on the photoreceptive surface 14a, and the cover 12 is closed. In the closed position, the cover 12 covers up the photoreceptive surface 14a and the subject on the photoreceptive surface 14a light-tightly. The sealing member 17 enhances the light-tightness and air-tightness of the internal space of the image scanning apparatus 2.

After the cover 12 is closed, a start command for starting image-capturing is sent from the external apparatus 36 to the image scanning apparatus 2. The start command is fed through the data transfer section 34 to the controller 30. As an alternative, the start command may be entered by operating a start button that may be provided on the base 10.

In response to the start command, the controller 30 turns the ultraviolet fluorescent tubes 16 on to irradiate the subject with the ultraviolet rays. As being fluorochrome-labeled, the subject is excited by the ultraviolet rays, radiating fluorescent light of such amount that corresponds to the reaction of the biological substances. The controller 30 measures the elapse of time from the start of lighting of the ultraviolet fluorescent tubes 16, and turns off the ultraviolet fluorescent tubes 16 when a predetermined time is over.

After turning off the ultraviolet fluorescent tubes 16, the controller 30 sends the drive signal to the image sensor 14. In accordance with the drive signal, the image sensor 14 captures the fluorescent light from the subject to output analog image signals. As having the near-infrared sensitive photoelectric conversion layer 50, the red sensitive photoelectric conversion layer 51, the green sensitive photoelectric conversion layer 52 and the blue sensitive photoelectric conversion layer 53, the image sensor 14 output RGB image signals and near-infrared image signal.

The analog image signals are converted through the A/D converter 32 into digital image data. The image data is transferred through the data transfer section 34 to the external apparatus 36. On the basis of the obtained image data, it is possible to carry out analyses of the biological substances contained in the subject.

As described above, since the image scanning apparatus 2 captures the image of the subject while placing the subject directly on the photoreceptive surface 14a of the image sensor 14, the image sensor 14 does not suffer from light attenuation through an optical system, and thus captures an image with high-sensitivity. Because the sensitivity to the chemiluminescent or fluorescent light is improved, the image sensor 14 needs a shorter exposure time. Furthermore, imaging the subject in direct contact with the photoreceptive surface 14a makes it unnecessary to form an image of the subject through an optical system, which saves the internal space for the optical system in the perpendicular direction to the photoreceptive surface 14a, so the image scanning apparatus 2 can be made thinner.

Figure 6:
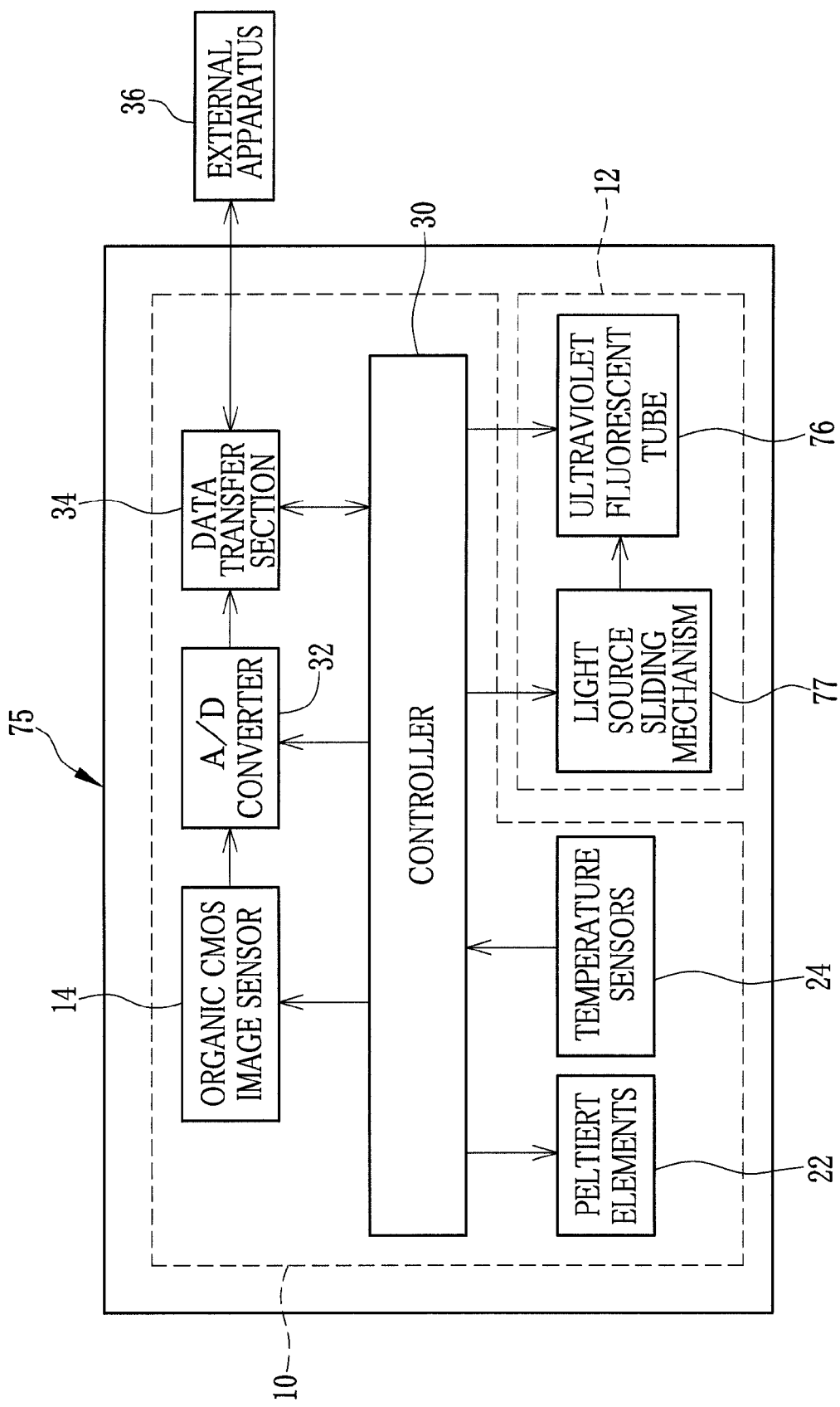
FIG. 6 is a block diagram of an image scanning apparatus provided with a mechanism for carrying a light source.

In the above embodiment, numbers of ultraviolet fluorescent tubes 16 are mounted on the inside of the cover 12 in order to illuminate the whole area of the photoreceptive surface 14a with a uniform amount of ultraviolet rays. It is alternatively possible to provide a single ultraviolet fluorescent tube 76 and a light source sliding mechanism 77 for sliding the ultraviolet fluorescent tube 76 across the inside surface of the cover 12, as shown in FIG. 6. An image scanning apparatus 75 of FIG. 6 is configured equivalently to the image scanning apparatus 2, except the ultraviolet fluorescent tube 76 and its sliding mechanism 77, so the detail of other components will be omitted.

For example, the ultraviolet fluorescent tube 76 is supported at its opposite ends by not-shown rails that are mounted on the inside surface of the cover 12, so that the ultraviolet fluorescent tube 76 may slide across from one end to the other end of the inside surface of the cover 12. The light source sliding mechanism 77 is driven by a control signal from a controller 30, to slide the ultraviolet fluorescent tube 76 at a constant speed.

As the light source sliding mechanism 77 is driven in the closed position of the cover 12, the ultraviolet fluorescent tube 76 slides in parallel to the photoreceptive surface 14a. Thus, the ultraviolet fluorescent tube 76 illuminates the whole area of the photoreceptive surface 14a uniformly as it slides at the constant speed in the closed position of the cover 12. The light source sliding mechanism 77 may be a well-known mechanism such as a rack and pinion mechanism or a ball screw mechanism.

Figure 7:
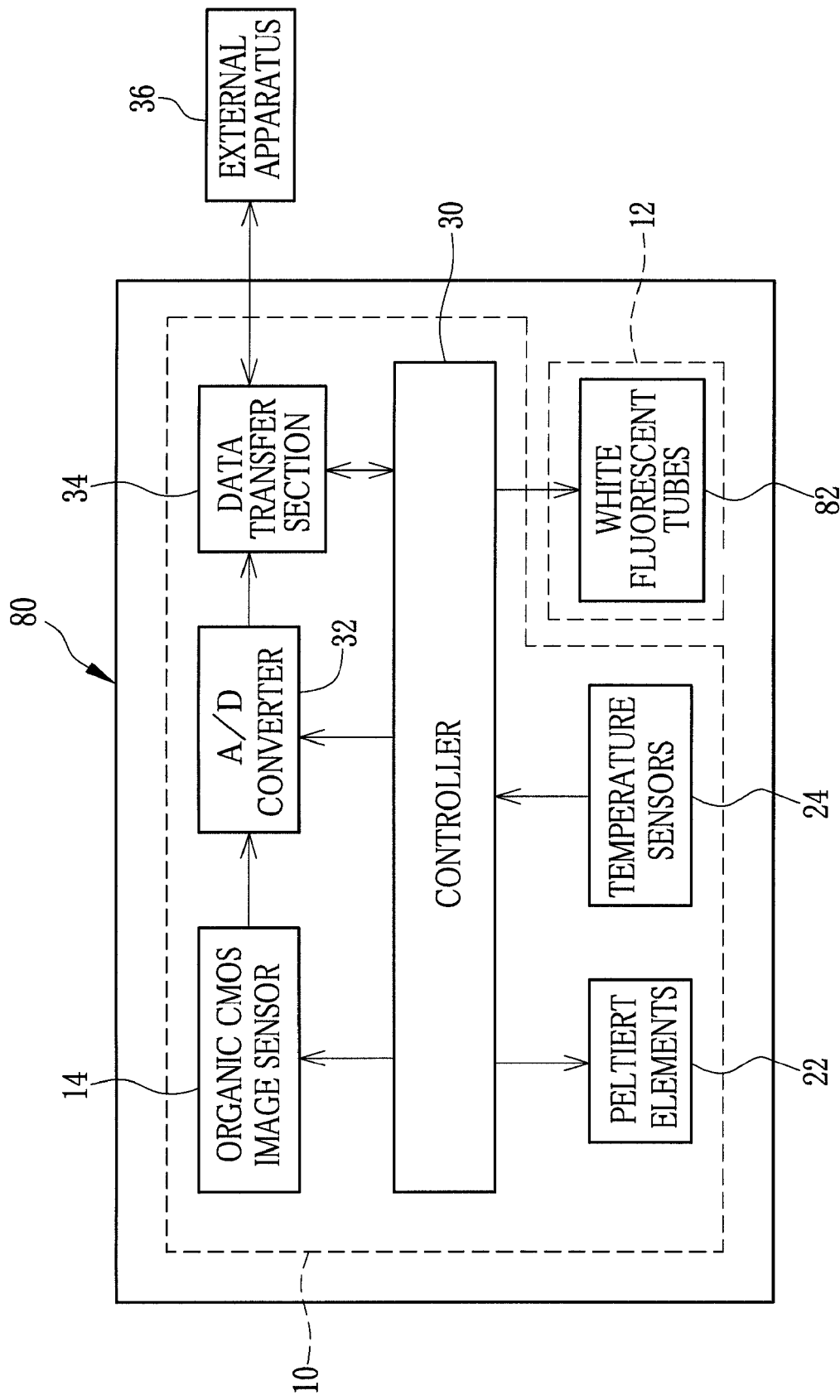
FIG. 7 is a block diagram of an image scanning apparatus provided with a white fluorescent tube.

In the above embodiment, the ultraviolet fluorescent tubes 16 or the ultraviolet fluorescent tube 76 is used as the light source for capturing an image from the fluorochrome-labeled subject. Instead of the ultraviolet fluorescent tubes 16 or the ultraviolet fluorescent tube 76, it is possible to use a plural number of white fluorescent tubes 82 as a light source, as shown in an image scanning apparatus 80 of FIG. 7. Like the ultraviolet fluorescent tubes 16, the white fluorescent tubes 82 are mounted on an inside surface of a cover 12 so as to oppose to a photoreceptive surface 14a in a closed position of the cover 12. In order to illuminate the whole area of the photoreceptive surface 14a uniformly with the white light, the white fluorescent tubes 82 are arranged at equal intervals.

The image scanning apparatus 80 captures an image from a subject that is dyed with an appropriate dye, e.g. Coomassie brilliant blue (CBB) dye, by illuminating the subject with the white light from the white fluorescent tubes 82 and detecting light transmitted through the subject by an organic CMOS image sensor 14. Thereby, the captured image has a density distribution that represents reaction of biological substances contained in the subject.

Figure 8:
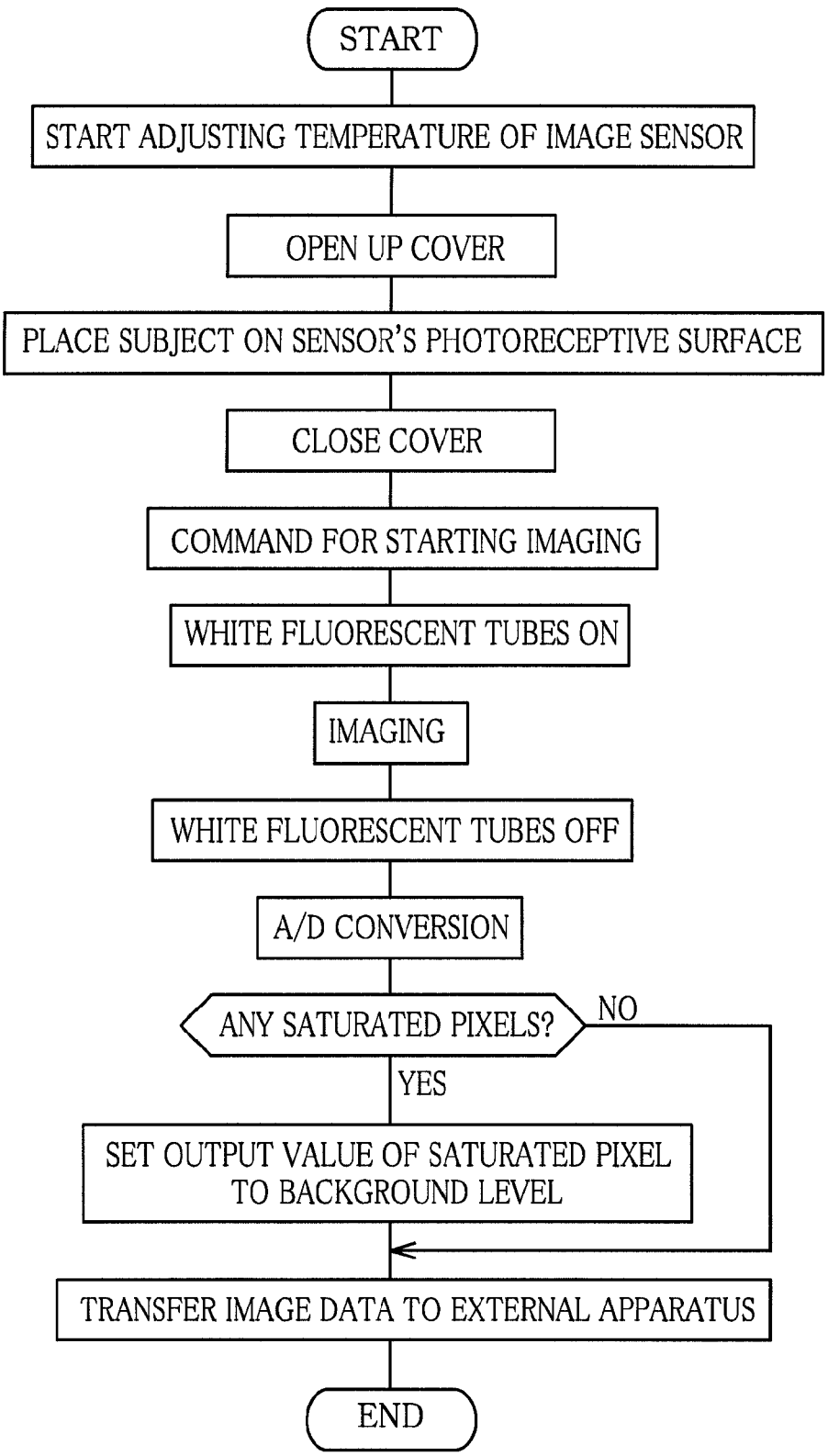
FIG. 8 is a flowchart illustrating a sequence of procedures for capturing an image of a dyed subject.

Next the procedure of image-capturing by the image scanning apparatus 80 will be described with reference to the flowchart of FIG. 8. When, for example, the image scanning apparatus 80 is powered on, a controller 30 of the image scanning apparatus 80 starts adjusting temperature of the image sensor 14 by use of peltiert elements 22 and temperature sensors 24. Thereafter when a start command for starting image-capturing is input, for example, through an external apparatus 36, the controller 30 turns the white fluorescent tubes 82 on, and sends a drive signal to the image sensor 14. According to the drive signal, the image sensor 14 detects the light transmitted through the subject, to obtain analog image signals. The controller 30 turns off the white fluorescent tubes 82 when a given exposure time is over.

The analog image signals are converted through an A/D converter 32 into digital image data. The A/D converter 32 checks individual pixels of the digital image data whether any of them are saturated or not, that is, whether any of them have a maximum digital value. Because those pixels, which detect the white light falling on the image sensor 14 directly from the white fluorescent tubes 82 or through non-dyed portions of the subject, are saturated, the image data of the saturated pixels are not necessary for analysis of the biological substances contained in the subject.

For this reason, the A/D converter 32 sets the maximum output value of the saturated pixels to a background level, i.e. an output value of all pixels in a complete dark space. The A/D converter 32 of the image scanning apparatus 80 corresponds to an image processing device recited in the appended claims. Note that the A/D converter 32 should not necessarily set the maximum output value of the saturated pixels to the background level, but may set it to an appropriate value less than the maximum value.

After the A/D conversion and the discrimination of the saturated pixels, the image data is sent through a data transfer section 34 to the external apparatus 36. This way, the image scanning apparatus 80 captures an image from the dyed subject, using the white light. As the white light source, other devices than the white fluorescent tubes 82 are applicable insofar as they are suitable for illuminating the dyed subject.

Furthermore, the image scanning apparatus 80 can also capture an image from a chemiluminescent subject by imaging without lighting the white fluorescent tubes 82. It is also possible to capture two kinds of images from a subject that has dyed portions and chemiluminescent portions by imaging while illuminating with the white light and without the illumination. The images captured from the dyed portions and chemiluminescent portions of the same subject may be composed into an image.

Figure 9:
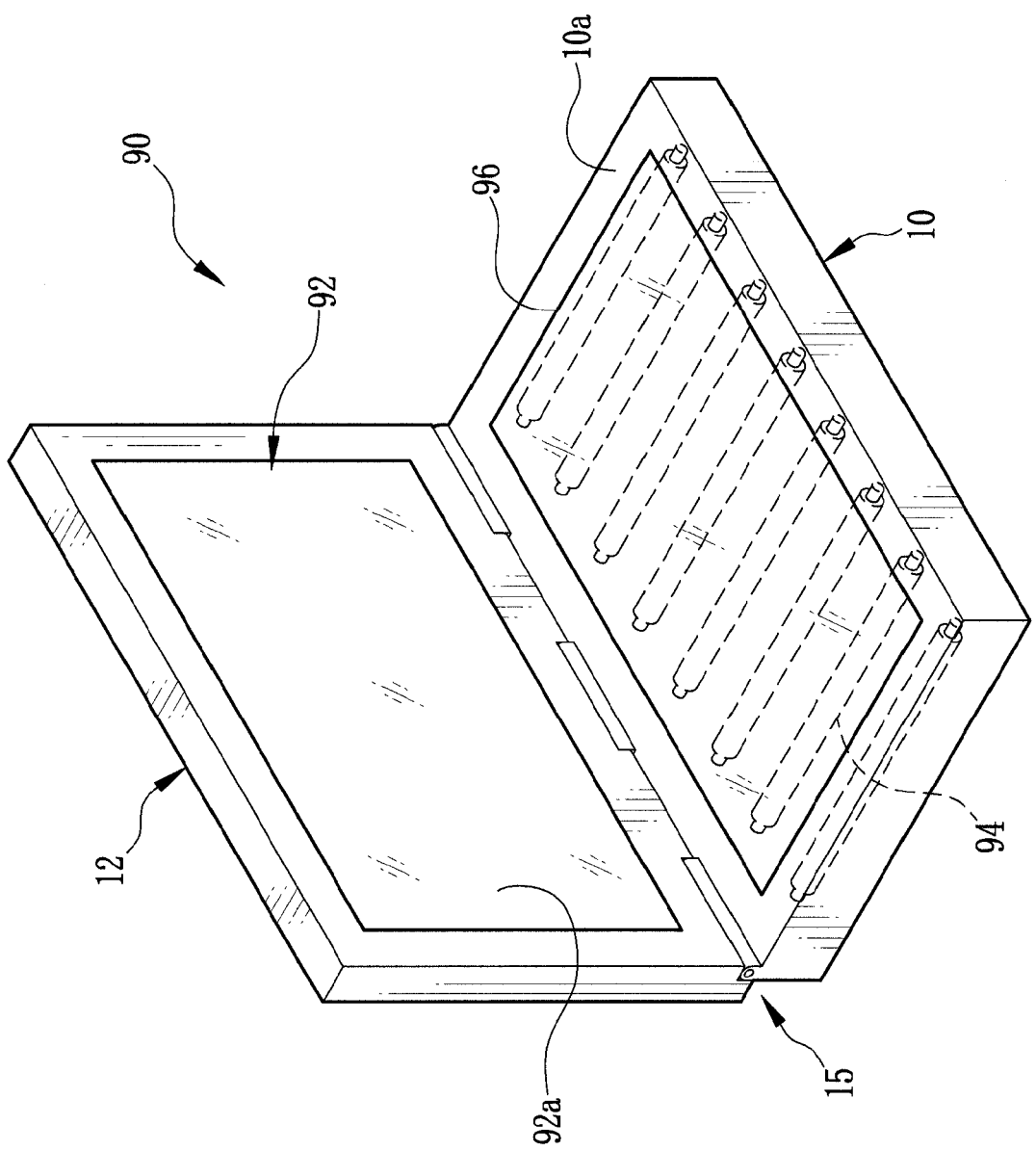
FIG. 9 is a perspective view illustrating an image scanning apparatus that has an image sensor mounted on its cover.

Although the image sensor 14 is mounted in the base 10 in the above embodiments, it is possible to mount an organic CMOS image sensor 92 in a cover 12 as shown in an image scanning apparatus 90 of FIG. 9. A photoreceptive surface 92a of the organic CMOS image sensor 92 is exposed on an inside surface of the cover 12.

On the other hand, a base 10 of the image scanning apparatus 90 is provided with a plural number of light source members 94 and a light permeable plate 96. The light source members 94 are arranged at equal intervals inside the base 10, and covered with the light permeable plate 96. The light permeable plate 96 is for supporting a subject, and letting light from the light source members 94 pass through it to illuminate the subject. The light source members 94 may emit excitation light or white light. The light permeable plate 96 may be made of transparent glass, a transparent resin material, or a milk white resin material that transmits and diffuses the light.

When the cover 12 is closed, the photoreceptive surface 92a gets into contact with an obverse surface of the light permeable plate 96. Thus, the subject placed on the light permeable plate 96 is brought into contact with the photoreceptive surface 92a in the closed position of the cover 12, in which the image sensor 92 is driven to capture an image from the subject by scanning the whole area of the photoreceptive surface 92a. As the subject is in direct contact with the photoreceptive surface 92a during the imaging, the same effect is achieved as the above-described embodiment even where the image sensor 92 is mounted in the cover 12. Although the subject is illuminated with light that is projected from the light source members 94 through the light permeable plate 96 in the embodiment shown in FIG. 9, it is possible to use a sheet type light source like an organic EL (organic light emitting display) and place a subject directly on the sheet type light source.

Figure 10:
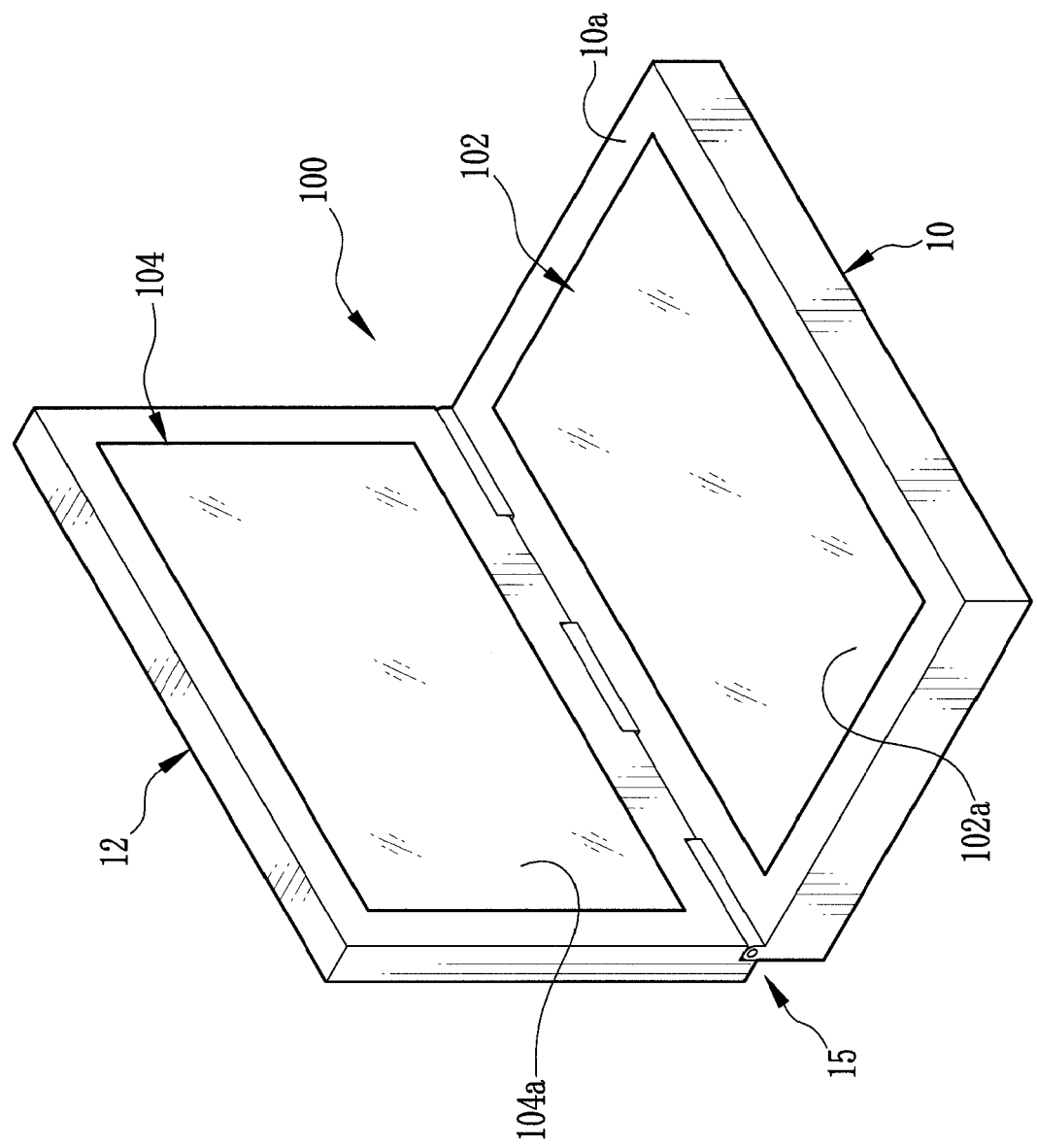
FIG. 10 is a perspective view illustrating an image scanning apparatus that has first and second image sensors mounted on its cover and base respectively.

Furthermore, it is possible to mount image sensors both in a base 10 and in a cover 12, like in an image scanning apparatus 100 as shown in FIG. 10. The image scanning apparatus 100 has a first organic CMOS image sensor 102 mounted in the base 10, and a second organic CMOS image sensor 104 mounted in the cover 12. The first organic CMOS image sensor 102 has its photoreceptive surface 102a exposed on a top surface of the base 10, whereas the second organic CMOS image sensor 104 has its photoreceptive surface 104a exposed on an inside surface of the cover 12. The photoreceptive surfaces 102a and 104a of the image sensors 102 and 104 are brought into contact with each other when the cover 12 is closed.

For image-capturing, a subject is placed directly on the photoreceptive surface 102a of the first image sensor 102, and the cover 12a is closed to bring the photoreceptive surface 104a of the second image sensor 104 into contact with the photoreceptive surface 102a. Then the image sensors 102 and 104 are driven to obtain first and second image data from the subject respectively.

Figure 11:
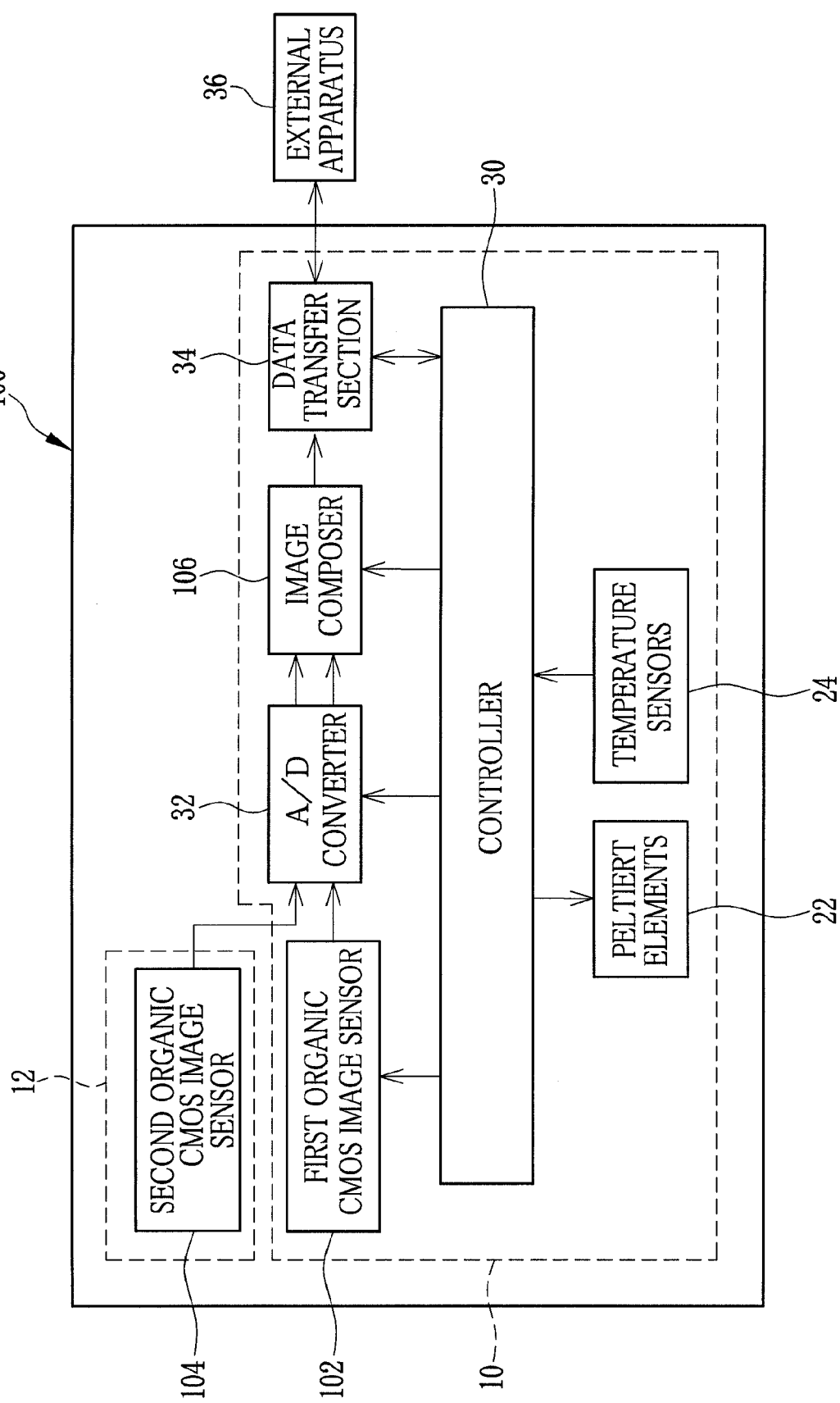
FIG. 11 is a block diagram illustrating an electric structure of the image scanning apparatus of FIG. 10.

The image scanning apparatus 100 also has an image composer 106 that is mounted for example in the base 10, as shown in FIG. 11. An analog image signal from the first image sensor 102 and an analog image signal from the second image sensor 104 are converted through an A/D converter 32 into first and second digital image data respectively. Then, the image composer 106 adds output values of each pair of counterpart pixels of the first and second image sensors 102 and 104, to unite the first and second image data into a set of composite image data. The composite image data is sent through a data transfer section 34 to an external apparatus 36.

As the subject is in direct contact with the photoreceptive surface 102a and 104a during the imaging, the embodiment of FIG. 10 achieves the same effect as the above embodiment. In addition to that, since two sets of image data obtained from opposite sides of the subject are composed into a set of image data, the image scanning apparatus 100 shown in FIG. 10 is improved in sensitivity to chemiluminescent light from the subject.

Figure 12:
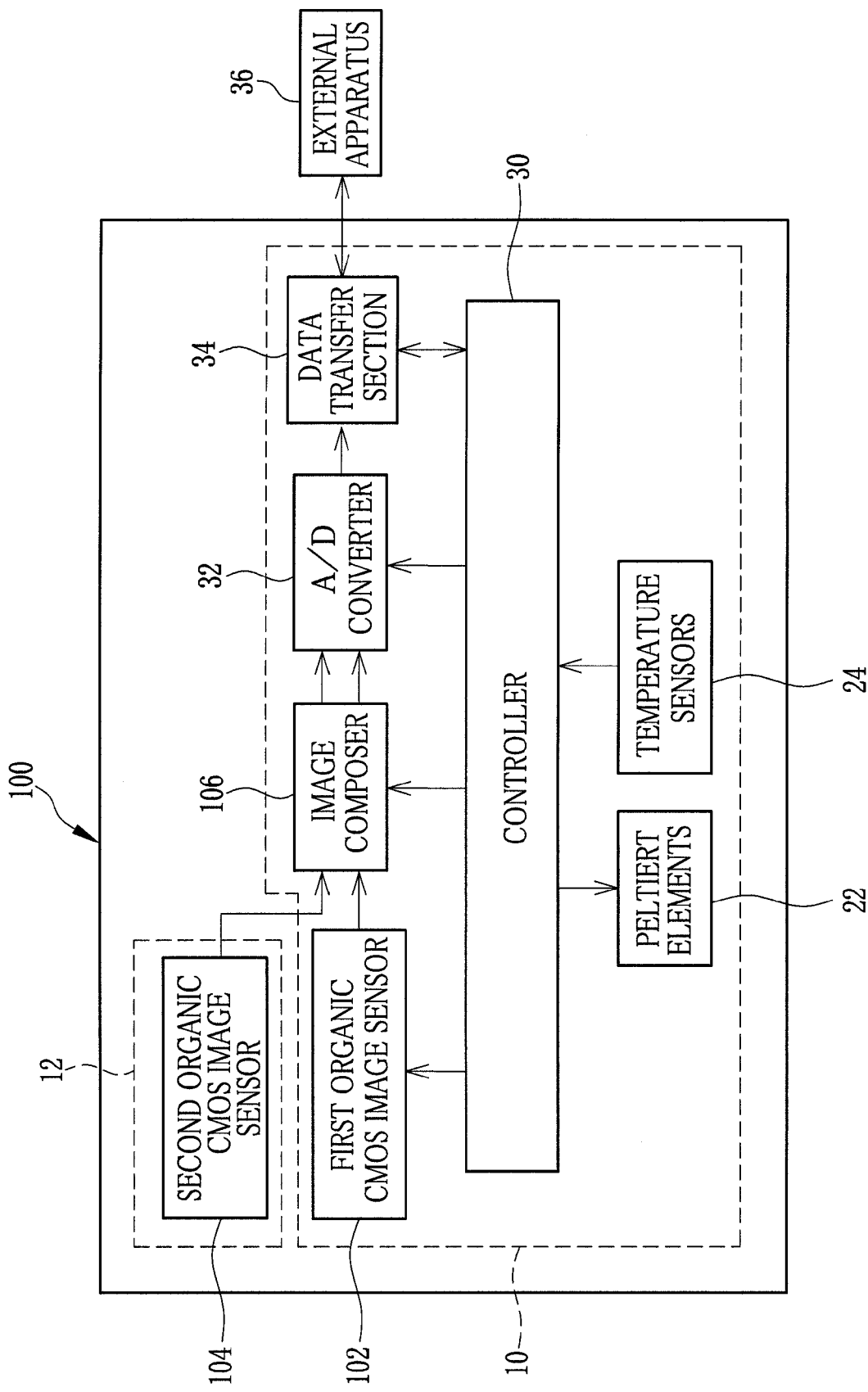
FIG. 12 is a block diagram illustrating an electric structure of an image scanning apparatus that synthesizes analog image signals from the first and second image sensors.

In the embodiment shown in FIG. 11, the image composer 106 is connected behind the A/D converter 32, to compose the first and second digital image data from the A/D converter 32. It is alternatively possible to connect an image composer 106 before the A/D converter 32 as shown in FIG. 12, to compose the analog image signals from the first and second image sensors 102 and 104.

Because the image scanning apparatus 100 is not provided with any light source, it can image only chemiluminescent subjects. In order to make it possible to image fluorochrome-labeled or dyed subjects, a light emitting portion like an LED array may be formed on a silicone substrate 40 beside photoelectric conversion layers 42 of either of the organic CMOS image sensors 102 and 104, so that the respective photoreceptive surfaces 102a and 104a may emit light.

Although the above embodiments use four-layer organic CMOS image sensors for obtaining RGB image data and NIR (near-infrared) image data, the image scanning apparatus of the present invention may use other kinds of image sensors. For example, the image sensor may have a triple-layer structure, a double-layer structure or a monolayer structure. In the case of triple-layer structure, respective layers may be obtaining RGB image signals, or NIR, R and G image signals. The image sensors are not to be limited to CMOS type, but may be CCD type or another type.

Furthermore, the image sensor applicable to the image scanning apparatus of the present invention is not limited to an organic imaging device having organic photoelectric conversion layers. For example, a conventional inorganic image sensor having Bayer-arranged color filters or a hybrid imaging sensor having organic and inorganic imaging devices in combination is applicable. However, because the inorganic image sensor is difficult to have a large area from an aspect of production process for semiconductors, it is preferable to use an organic image sensor for the purpose of producing a photoreceptive surface of 10 cm×15 cm or more. As described above, the area size of the photoreceptive surface of the image sensor is not specifically limited, but preferably not less than 10 cm×15 cm, because such a large-size photoreceptive surface makes it possible to place a micro titer plate having 96 wells directly on the photoreceptive surface and carry out imaging of reagent solutions put in the respective wells. This widens application range of the image scanning apparatus of the present invention.

Although the above embodiment uses the SELFOC lens array 46 as the protection layer, the protection layer is not limited to this embodiment, but may for example be a micro capillary plate, a diamond thin film, a metal oxide film, metal nitride film, fluororesin, poly paraxylene, silicone resin, polystyrene resin, or light curing resin.

Although the cover 12 is hinged to the base 10 in the above embodiments, the cover 12 may be mounted to slide on the base 10 between an open position and a closed position. It is also possible to form the cover 12 as a separate member from the base 10.

Although the above embodiments use the ultraviolet fluorescent tubes 16 or 76, or the white fluorescent tubes 82 as the light source, the light source is not limited to these embodiments, but may be a well-known light source, such as LED, laser diode, or a halogen lamp combined with a diffusion plate, insofar as it can excite or illuminate the subject. To control the temperature of the image sensor, the peltiert elements 22 and the temperature sensors 24 are used in the above embodiment. But the temperature of the image sensor may be controlled by use of other devices, e.g. a heat exchanger that circulates temperature-controlled liquid or gas, or an electric heater.

Thus, the present invention is not to be limited to the above embodiments but, on the contrary, various modifications will be possible without departing from the scope of claims appended hereto.

What is claimed is:

1. An image capturing apparatus for capturing an image from a subject containing biological substances, the image representing reaction of said biological substances, said image capturing apparatus comprising:
   a base having a supporting side for supporting the subject thereon;
   an image sensor having a photoreceptive surface and at least a photoelectric conversion layer that generates electric charge corresponding in amount to light entering from said photoreceptive surface, said image sensor being mounted in said base with said photoreceptive surface exposed on the supporting side of said base, so the subject placed on the supporting side is in contact with said photoreceptive surface;
   a cover for covering up said photoreceptive surface in a light-tight fashion; and
   further comprising a light source mounted in said cover, said light source being opposed to said photoreceptive surface and emitting light toward said photoreceptive surface while said cover is in a closed position covering up said photoreceptive surface, wherein said light source comprises a light source member and a mechanism for moving said light source member at a constant speed in parallel to said photoreceptive surface in the closed position of said cover, to illuminate the whole area of said photoreceptive surface uniformly.

2. An image capturing apparatus as recited in claim 1, wherein the biological substances of the subject are labeled with a fluorescent pigment, and said light source emits excitation light toward the subject, whereas said image sensor captures an image from fluorescent light that is radiated from the biological substances as being excited by said excitation light.

3. An image capturing apparatus as recited in claim 2, wherein said image sensor comprises a band elimination filter for cutting only a wavelength band of said excitation light.

4. An image capturing apparatus as recited in claim 1, further comprising a temperature adjusting device for adjusting said image sensor to a set temperature.

5. An image capturing apparatus as recited in claim 4, wherein said base is provided with a hollow on a back side of said image sensor, and said temperature adjusting device comprises a plural number of peltiert elements and temperature sensors, which are arranged in an array on a top surface of said hollow that corresponds to the back side of said image sensor.

6. An image capturing apparatus for capturing an image from a subject containing biological substances, the image representing reaction of said biological substances, said image capturing apparatus comprising:

a base having a supporting side for supporting the subject thereon;

an image sensor having a photoreceptive surface and at least a photoelectric conversion layer that generates electric charge corresponding in amount to light entering from said photoreceptive surface, said image sensor being mounted in said base with said photoreceptive surface exposed on the supporting side of said base, so the subject placed on the supporting side is in contact with said photoreceptive surface;

a cover for covering up said photoreceptive surface in a light-tight fashion; and further comprising a light source mounted in said cover, said light source being opposed to said photoreceptive surface and emitting light toward said photoreceptive surface while said cover is in a closed position covering up said photoreceptive surface, wherein said light source emits white light toward said photoreceptive surface, and said image sensor captures an image from light transmitted through the subject as placed on said photoreceptive surface.

7. An image capturing apparatus as recited in claim 6, further comprising an image processing device for discriminating saturated pixels of said image sensor after the image-capturing, and setting an output value of the saturated pixels to a predetermined level.

8. An image capturing apparatus for capturing an image from a subject containing biological substances, the image representing reaction of said biological substances, said image capturing apparatus comprising:

a base having a supporting side for supporting the subject thereon;

an image sensor having a photoreceptive surface and at least a photoelectric conversion layer that generates electric charge corresponding in amount to light entering from said photoreceptive surface, said image sensor being mounted in said base with said photoreceptive surface exposed on the supporting side of said base, so the subject placed on the supporting side is in contact with said photoreceptive surface; and a cover for covering up said photoreceptive surface in a light-tight fashion, wherein said photoelectric conversion layer of said image sensor is an organic photoelectric conversion layer.

9. An image capturing apparatus as recited in claim 8, wherein said image sensor comprises a plural number of said organic photoelectric conversion layers, which are sensitive to light components of different wavelength ranges from one layer to another.

10. An image capturing apparatus as recited in claim 9, wherein said organic photoelectric conversion layers are stacked in such a sequence that one sensitive to the shorter wavelength range is located closer to said photoreceptive surface.

11. An image capturing apparatus as recited in claim 9, wherein said organic photoelectric conversion layers are respectively sensitive to near-infrared light, red light, green light and blue light, so said image sensor outputs near-infrared, red, green and blue image signals.

12. An image capturing apparatus as recited in claim 8, wherein said image sensor has a protection layer to protect said organic photoelectric conversion layer.

13. An image capturing apparatus for capturing an image from a subject containing biological substances, the image representing reaction of said biological substances, said image capturing apparatus comprising:

a base for supporting the subject on its supporting side;

a cover for covering up the supporting side of said base in a light tight fashion; and an image sensor having a photoreceptive surface and at least a photoelectric conversion layer that generates electric charge corresponding in amount to light entering from said photoreceptive surface, said image sensor being mounted in said cover so that said photoreceptive surface is in contact with the subject placed on the supporting side of said base when said cover is in a closed position covering up the supporting side of said base.

14. An image capturing apparatus as recited in claim 13, wherein said photoelectric conversion layer of said image sensor is an organic photoelectric conversion layer.

15. An image capturing apparatus as recited in claim 13, further comprising a light source mounted in said base, said light source being opposed to said photoreceptive surface and emitting light toward said photoreceptive surface while said cover is in the closed position.

16. An image capturing apparatus for capturing an image from a subject containing biological substances, the image representing reaction of said biological substances, said image capturing apparatus comprising:

a base for supporting the subject on its supporting side;

a cover for covering up the supporting side of said base in a light tight fashion;

a first image sensor mounted in said base with its photoreceptive surface exposed on the supporting side of said base, said first image sensor having at least an organic photoelectric conversion layer to output a first analog image signal corresponding to a light component received from the subject that is placed on said supporting side in contact with said photoreceptive surface; and a second image sensor mounted in said cover so that said photoreceptive surface is brought into contact with the subject placed on the supporting side of said base when said cover is set to a closed position covering up the supporting side of said base, said second image sensor having at least an organic photoelectric conversion layer to output a second analog image signal corresponding to a light component received from the subject.

17. An image capturing apparatus as recited in claim 16, further comprising a device for producing a digital composite image from said first and second analog image signals.

18. An image capturing method using an image sensor having at least an organic photoelectric conversion layer for capturing an image from a subject containing biological substances, the image representing reaction of said biological substances, said image capturing method comprising steps of:

placing the subject on a supporting side of a base;

bringing a cover to a closed position covering up the supporting side of said base in a light tight fashion; and driving said image sensor in the closed position of said cover, said image sensor being mounted in at least one of said base and said cover so that a photoreceptive surface of said image sensor is in contact with the subject in the closed position of said cover.

19. An image capturing method as recited in claim 18, further comprising a step of adjusting temperature of said image sensor to a predetermined range in advance to said driving step.

* * * * *